(12) United States Patent
Nawrocki et al.

(10) Patent No.: US 8,747,436 B2
(45) Date of Patent: Jun. 10, 2014

(54) BI-DIRECTIONAL BARBED SUTURE

(75) Inventors: Jesse G. Nawrocki, Annandale, NJ (US); David C. Lindh, Sr., Flemington, NJ (US); J. Jenny Yuan, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 1732 days.

(21) Appl. No.: 11/762,141

(22) Filed: Jun. 13, 2007

(65) Prior Publication Data
US 2008/0312688 A1   Dec. 18, 2008

(51) Int. Cl.
A61B 17/04 (2006.01)

(52) U.S. Cl.
USPC .................................................. 606/228

(58) Field of Classification Search
USPC ............ 606/224, 228, 229, 219, 220; 24/442, 24/445, 447, 449; 428/364, 400; 132/321
See application file for complete search history.

(56) References Cited

U.S. PATENT DOCUMENTS

| | | | |
|---|---|---|---|
| 3,123,077 A | | 3/1964 | Alcamo |
| 3,522,637 A | * | 8/1970 | Brumlik .......................... 24/445 |
| 3,700,544 A | | 10/1972 | Matsui |
| 3,716,058 A | | 2/1973 | Tanner, Jr. |
| 3,720,055 A | | 3/1973 | DeMestral et al. |
| 3,833,972 A | | 9/1974 | Brumlik |
| 3,845,641 A | | 11/1974 | Waller |
| 3,981,051 A | | 9/1976 | Brumlik |
| 4,541,154 A | * | 9/1985 | Ito et al. .......................... 24/442 |
| 4,548,202 A | | 10/1985 | Duncan |
| 4,900,605 A | | 2/1990 | Thorgersen et al. |
| 5,269,783 A | | 12/1993 | Sander |
| 5,342,376 A | | 8/1994 | Ruff |
| 5,395,126 A | | 3/1995 | Tresslar |
| 5,425,747 A | | 6/1995 | Brotz |
| 5,584,859 A | | 12/1996 | Brotz |
| 5,931,855 A | | 8/1999 | Buncke |
| 5,964,783 A | | 10/1999 | Grafton et al. |

(Continued)

FOREIGN PATENT DOCUMENTS

| | | |
|---|---|---|
| DE | 1810800 | 6/1970 |
| EP | 0831763 B1 | 10/2001 |

(Continued)

OTHER PUBLICATIONS

Dattilo, P.P. Jr., et al., "Tissue Holding Performance of Knotless Absorbable Sutures", Society for Biomaterials 29th Annual Meeting Transactions (2003) p. 101.

(Continued)

*Primary Examiner* — Corrine M McDermott
*Assistant Examiner* — Alexander Orkin

(57) ABSTRACT

Surgical sutures having a core extending along a length thereof between a first end and a second end, and a plurality of sets of first and second projections, wherein the first projections extend in a direction of a first end of the suture and the second projections extend in a direction of a second end of the suture. The first projections may be sized and shaped, and positioned relative to the second projections so as to be capable of substantially shielding the second projections when the surgical suture is drawn through tissue by the second end thereof. The first projections may additionally or alternatively be capable of overlapping and substantially covering a distal end of the respective second projections when the suture is drawn through tissue by the second end.

19 Claims, 3 Drawing Sheets

(56) References Cited

U.S. PATENT DOCUMENTS

| | | |
|---|---|---|
| 6,162,537 A | 12/2000 | Martin et al. |
| 6,241,747 B1 | 6/2001 | Ruff |
| 6,270,517 B1 | 8/2001 | Brotz |
| 6,367,128 B1 * | 4/2002 | Galkiewicz et al. ......... 24/585.1 |
| 6,599,310 B2 | 7/2003 | Leung et al. |
| 6,624,097 B2 | 9/2003 | Martin et al. |
| 6,848,152 B2 | 2/2005 | Genova et al. |
| 7,070,610 B2 | 7/2006 | Im et al. |
| 2001/0023020 A1 | 9/2001 | Martin et al. |
| 2003/0001407 A1 | 1/2003 | Hoshikawa et al. |
| 2003/0041426 A1 | 3/2003 | Genova et al. |
| 2003/0074023 A1 | 4/2003 | Kaplan et al. |
| 2003/0149447 A1 | 8/2003 | Morency et al. |
| 2004/0009028 A1 | 1/2004 | Gueret |
| 2004/0060409 A1 | 4/2004 | Lleung et al. |
| 2004/0060410 A1 | 4/2004 | Leung et al. |
| 2004/0088003 A1 | 5/2004 | Leung et al. |
| 2004/0093028 A1 | 5/2004 | Ruff |
| 2004/0193191 A1 | 9/2004 | Starksen et al. |
| 2005/0118388 A1 | 6/2005 | Kingsford |
| 2005/0203576 A1 | 9/2005 | Sulamanidze et al. |
| 2005/0234510 A1 * | 10/2005 | Zamierowski ................ 606/215 |
| 2005/0240224 A1 | 10/2005 | Wu |
| 2005/0267531 A1 * | 12/2005 | Ruff et al. .................... 606/228 |
| 2006/0079935 A1 | 4/2006 | Kolster |
| 2006/0135994 A1 | 6/2006 | Ruff et al. |
| 2006/0135995 A1 | 6/2006 | Ruff et al. |
| 2007/0005110 A1 | 1/2007 | Collier et al. |
| 2009/0012560 A1 * | 1/2009 | Hunter et al. ................. 606/228 |

FOREIGN PATENT DOCUMENTS

| | | |
|---|---|---|
| EP | 1075843 B1 | 2/2005 |
| EP | 1429664 B1 | 3/2007 |
| GB | 1091282 | 11/1967 |
| JP | 2003339849 | 12/2003 |
| WO | WO 96/06565 A1 | 3/1996 |
| WO | WO 00/16715 A1 | 3/2000 |
| WO | WO 03/017850 A2 | 3/2003 |
| WO | WO 03/044253 A1 | 5/2003 |
| WO | WO 03/083191 | 10/2003 |
| WO | WO 2004/030520 A2 | 4/2004 |
| WO | WO 2004/030704 A2 | 4/2004 |
| WO | WO 2004/030705 A | 4/2004 |
| WO | WO 2006/005144 A1 | 1/2006 |
| WO | WO 2006/061868 A1 | 6/2006 |

OTHER PUBLICATIONS

McKenzie, A.R., "An Experimental Multiple Barbed Suture for the Long Flexor Tendons of the Palm and Fingers", The Journal of Bone and Joint Surgery, (1967) vol. 49B, No. 3, pp. 440-447.

Schmid, A. et al., "The outspreading anchor cord". A material for anthroscopic suturing of a fresh anterior cruciate ligament rupture.

* cited by examiner

FIG. 4a      FIG. 4b

BI-DIRECTIONAL BARBED SUTURE

FIELD OF THE INVENTION

The present invention is directed to barbed sutures and devices, and more particularly, to such sutures and devices having overlapping and opposing barbs.

BACKGROUND OF THE INVENTION

Barbed sutures have broad surgical applications, such as tissue approximation/plication, wound closure, and fixation of prosthetic devices to tissue. In vivo wound security, tissue compatibility, and scar cosmesis after wound repair are of particular interest to surgeons using barbed sutures.

For unidirectional barbed sutures having barbs facing in only a single direction, an anchor or knot is often used at the end to stop suture movement in the direction opposite to that in which the barbs face. Bi-directional barbed sutures typically have barbs facing in a first direction 101 on a first side of the suture, and barbs facing in the opposite direction 102 on a second side of the suture as shown in FIG. 1. Although these sutures resist movement in both directions, their insertion either requires some type of sheath or insertion device through which the suture is drawn (and which is later removed), or a double armed suture allowing the first end of the suture to be drawn through tissue with a first suture needle and the second end of the suture to be drawn through tissue with a second suture needle.

Double armed sutures, however, limit the wound closure or tissue approximation patterns that can be used. For example, the surgeon typically needs to begin suturing from the middle of the closure line out in two different directions. This technique may not always be acceptable to keep the appropriate tissue apposition.

When a sheath or tubular insertion tool is used, use of the suture is typically limited to procedures requiring short and in particular, straight placement. It is difficult for a surgeon to make several running stitches with a sheathed barbed suture due to the high frictional forces that accumulate along a torturous path. Further, when a surgeon tries to remove the sheath, the barbs as well as the surrounding tissue will likely be damaged.

Accordingly, there remains a need for a bi-directional barbed suture that can more readily and easily be inserted.

SUMMARY OF THE INVENTION

A surgical suture is provided having a core extending along a length thereof between a first end and a second end, and a plurality of sets of first and second projections extending from the core. The first projections extend toward the first end of the suture and the second projections extend toward the second end of the suture, and the first projections are capable of overlapping and substantially covering a distal end of the respective second projections when the suture is drawn through tissue by the second end.

According to various embodiments, the first projection may be larger than the second projection, and/or the first and second projections may be formed by cutting into the suture core. Further, the first and optionally the second projections may extend outwardly beyond an outermost dimension of the core. In yet another embodiment, the suture may be made from one of the following elements, or combinations thereof: polydioxanone, polyglactin, polyglycolic acid, copolymers of glycolide and lactide, polyoxaesters, poliglecaprone, polypropylene, polyethylene, polyvinylidene fluoride (PVDF), polyesters, polyethylene terephthalate, glycol-modified polyethylene terephthalate, polytetrafluoroethylene, fluoropolymers, nylons.

In yet another embodiment, the suture further includes one or more extensions projecting outwardly from an underside of the first and/or second projections.

Also provided is a surgical suture having a plurality of sets of first and second barbs. For each of the plurality of sets, the first barb extends toward a first end of the suture and the second barb extends toward a second end of the suture, and the first barb is capable of overlapping at least a distal end of the second barb.

The suture may further include a suture core, with the first and/or second barbs extending outwardly beyond an outermost dimension of the suture core. In an alternate embodiment, the first barbs extend outwardly beyond an outermost dimension of the suture core, and the second barbs do not extend outwardly beyond an outermost dimension of the suture core. In the latter embodiment, the second barbs may be formed by removing a portion of the suture core. Alternatively, the first and second barbs may be formed by cutting into the suture core.

In yet another embodiment, an underside of the first and/or second barbs further includes one or more extensions projecting outwardly therefrom.

In yet another embodiment, the surgical suture forms part of a braided surgical suture device. Optionally, the surgical suture forms a core of the braided surgical suture device.

Another surgical suture provided herein includes a core extending along a length thereof between a first end and a second end, and a plurality of sets of first and second projections. The first projections extend in a direction of a first end of the suture and the second projections extend in a direction of a second end of the suture, and the first projections are sized and shaped, and positioned relative to the second projections so as to be capable of substantially shielding the second projections when the surgical suture is drawn through tissue by the second end thereof.

In one embodiment, the first projections have a larger outer periphery than the respective second projections when viewed along a direction of the core. In yet another embodiment, an underside of the first and/or second projections has one or more extensions extending outwardly therefrom.

According to one alternate embodiment, the first projections substantially overlap at least a distal tip of the respective second projections when the suture is drawn through tissue by the second end thereof.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 2-4c illustrate various embodiments of a bi-directional suture according to the present invention;

DETAILED DESCRIPTION

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

Figure 1:
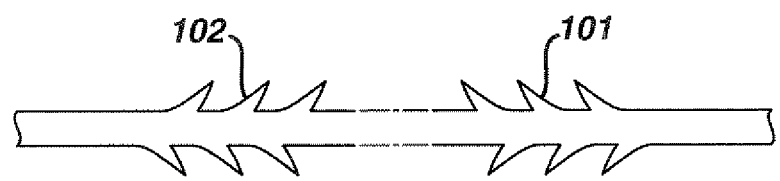
FIG. 1 illustrates an exemplary prior art bi-directional barbed suture.
Figure 2:
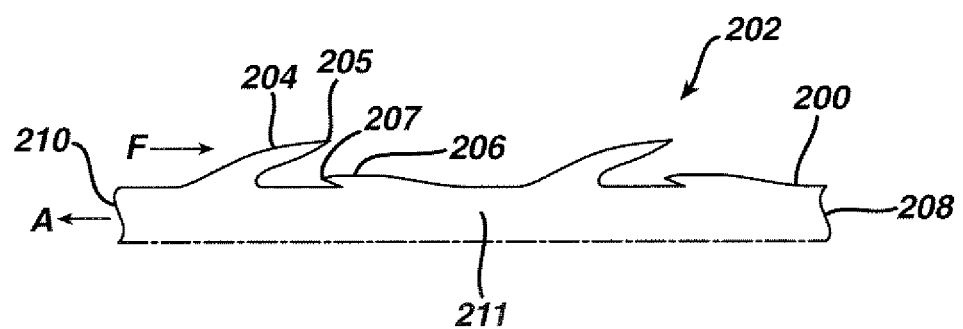

Referring now to FIGS. 2 and 2a, a surgical suture 200 according to the present invention includes a plurality of sets 202 of first 204 and second 206 projections or barbs (terms intended to be used interchangeably herein). For each of the sets 202 of projections, the first projection 204 extends to a distal end 205 in a direction of a first end 208 of the suture, and the second projection 206 extends to a distal end 207 in a direction of a second end 210 of the suture as shown. Thus, the first and second projections are opposed or facing opposite one another and thus capable of engaging tissue from opposing directions once in place within a patient.

According to one embodiment, the first projection is preferably larger than the second projection, but most importantly is positioned relative to the second projection so that its is capable of overlapping and substantially covering at least the distal tip 207 of the second projection 206 when the suture is being drawn through tissue by the first end 210 in the direction shown by arrow "A" of FIG. 2. When drawn through tissue in this manner, forces F will be exerted on the first projections 204, causing them to bend or somewhat flatten toward the suture core as shown in FIG. 2a, and in the process will overlap and substantially cover the distal tip 207 of the second projection 206 as is also shown in FIG. 2a. In this manner, the tissue grasping ability of the second projections is substantially neutralized as the suture is inserted, and thus, the suture can be drawn through tissue as if it were a uni-directional barbed suture. Once in position, however, when the first projections return towards their original position, such as will occur when surrounding tissue exerts its influence on the projections, the second projections will once again be effective to engage tissue, and the suture will better resist movement in the direction of both the first and second ends. Thus, the surgical suture described herein can readily and easily be inserted without requiring a double-armed suture or a separate sheath or insertion member, yet still provide the benefits of bi-directional barbs.

Figure 6:
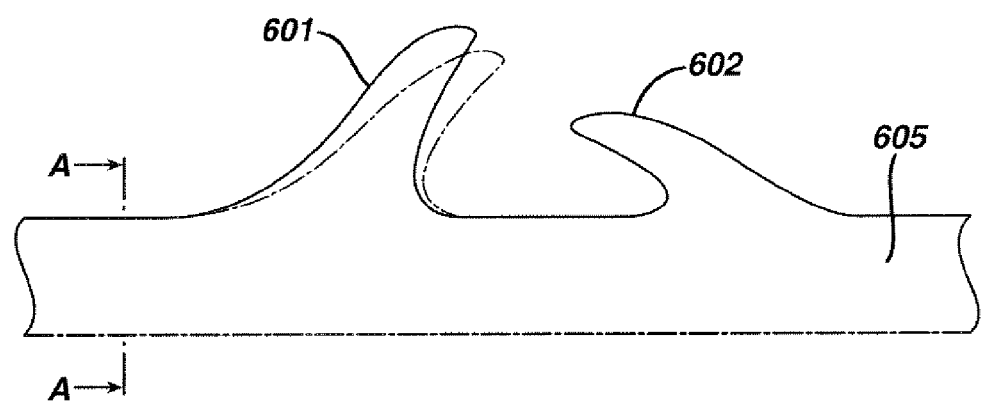
FIG. 6 illustrates an alternate embodiment of a bi-directional suture according to the present invention.
Figure 6A:
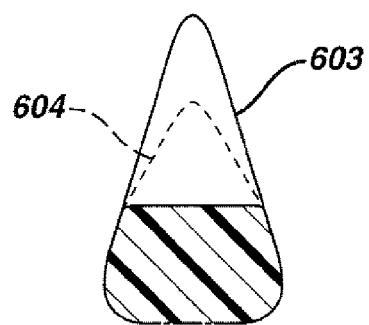
FIG. 6a illustrates a cross-section of the embodiment of FIG. 6 taken along line A-A of FIG. 6.

In an alternate embodiment, it is not necessary for the first projection to physically overlap and/or cover the distal tip of the second projection. As shown in the embodiment of FIGS. 6 and 6a, the first projection 601 has a larger outer profile or outer periphery 603 than the outer profile or periphery 604 of the second projection 602 when viewed in direction A-A along the suture shaft 605. Further, as shown in FIG. 6a, the second projection is positioned relative to the first projection so that the outer periphery of the second projection is behind and substantially hidden or shielded by the first projection when viewed in this direction. Where the first projection is sufficiently rigid or stiff so as to retain its ability to shield the second projection as the suture is drawn through tissue (see bending movement depicted in FIG. 6), the first projection will still substantially neutralize the second projection as described above, allowing the suture to be drawn through tissue as if it were a uni-directional barbed suture.

Figure 3:
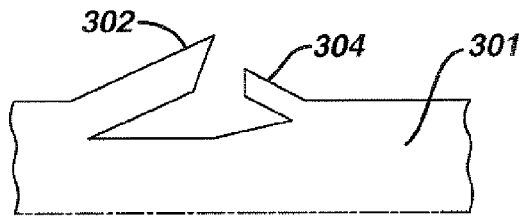
Figure 3:
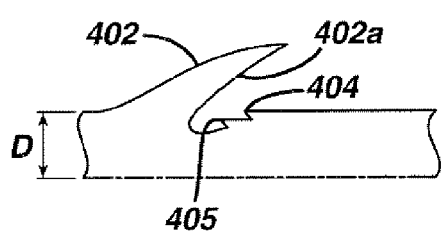
Figure 3:
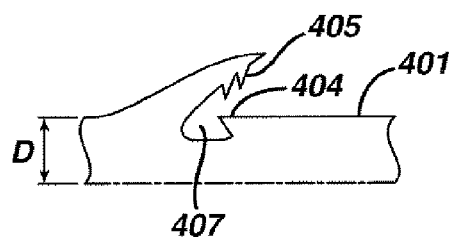

The embodiment described herein and various other configurations may be formed by any suitable technique, such as press-forming, profile punching, laser cutting or the like. Press-forming and profile punching techniques for forming sutures are described in detail in co-pending U.S. application Ser. No. 11/743,201, which is incorporated by reference in its entirety. FIG. 3 illustrates a similar embodiment wherein the first 302 and second 304 barbs or projections are formed entirely by cutting into the suture core or shaft 301 with a mechanical cutting element such as a blade.

Figure 4C:
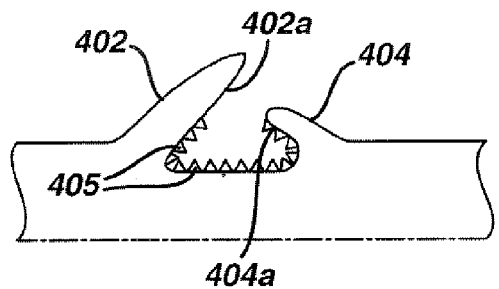

With reference now to FIGS. 4a-4c, the tissue holding ability of the suture may be enhanced by providing one or more extensions 405, such as can be achieved by a roughened or serrated surface, projecting outwardly from an underside 402a, 404a of the first 402 and/or second 404 projections or barbs. The serrations may take the form of miniature barbs or projections so as to enhance their ability to engage tissue. In the embodiment illustrated in FIG. 4a, the second projection (s) 404 do not extending outwardly beyond the outermost dimension D of the suture core 401, but rather define part of a recess 407 extending inwardly from the outermost dimension of the suture core. As indicated, press-forming, profile-punching or laser cutting are manufacturing techniques suitable for forming a suture having such a configuration.

Figure 5:
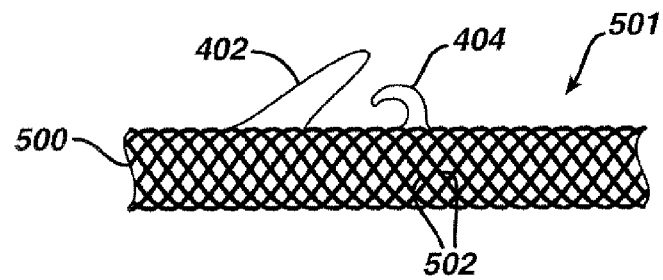
FIG. 5 illustrates a bi-directional suture according to the present invention incorporated within a braided suture device.

Finally, FIG. 5 illustrates a surgical suture 500 of the present invention that forms part of a braided surgical suture device 501. Braided surgical sutures are known in the art, and may consist of multiple surgical suture strands that are braided together, or that are braided around one or more filaments that form a core of the braided suture. In the embodiment of FIG. 5, a bi-directional suture of the present invention 500 forms the core, with multiple suture filaments 502 braided around the core whereby first and second projections extend outwardly through the braided filaments.

It will be apparent from the foregoing that, while particular forms of the invention have been illustrated and described, various modifications can be made without departing from the spirit and scope of the invention. For example, although particular barb configurations are illustrated and described herein, any suitable configuration and arrangement is possible within the scope of the invention so long as respective sets of barbs are capable of overlapping as described above. Further, although the embodiments illustrated and described herein show barbs on only one side of a suture, barbs may be positioned on any side, or multiple sides, and in any configuration (i.e., staggered around the suture shaft, multiple sets aligned around the suture shaft, randomly placed around the suture shaft). Accordingly, it is not intended that the invention be limited, except as by the appended claims.

What is claimed is:

1. A surgical suture comprising:
a monofilament core extending along a length thereof between a first end and a second end;
a plurality of sets of first and second projections extending outwardly from the core in a manner such that each set is longitudinally aligned along the length of the core, and positioned at different points along said length and between the first and second ends thereof, wherein the first projections extend outwardly from the core to a free distal end so as to point in a direction toward the first end of the suture and the second projections extend outwardly from the core to a free distal end so as to point in a direction toward the second end of the suture, and wherein the first projections extend outwardly from the core by a greater distance than the second projections, have an outer periphery greater than an outer periphery of the second projections and that substantially shields the outer periphery of the second projection when viewed along a longitudinal axis of the core, and are adapted to bend toward the second projections to overlap and sufficiently cover at least a distal portion of the respective second projections when the suture is drawn through tissue by the second end so as to substantially prevent the second projections from engaging tissue when drawn through said tissue.

2. The suture according to claim 1, wherein the first projection is larger than the second projection.

3. The suture according to claim 1, wherein the first and second projections are formed by cutting into the suture core.

4. The suture according to claim 1, wherein the first and second projections extend outwardly beyond an outermost dimension of the core.

5. The suture according to claim 1, wherein the first projections extend outwardly beyond an outermost dimension of the core, and the second projections do not extend outwardly beyond the outermost dimension of the core.

6. The suture according to claim 1, wherein the suture is comprised of a material selected from the group consisting of: polydioxanone, polyglactin, polyglycolic acid, copolymers of glycolide and lactide, polyoxaesters, poliglecaprone, polypropylene, polyethylene, polyvinylidene fluoride (PVDF), polyesters, polyethylene terephthalate, glycol-modified polyethylene terephthalate, polytetrafluoroethylene, fluoropolymers, nylons and combinations thereof.

7. The suture according to claim 1, further comprising one or more extensions projecting outwardly from an underside of at least one of the first and second projections.

8. A surgical suture comprising:
a plurality of sets of first and second barbs extending outwardly from a non-planar, monofilament suture core in a manner such that each set is longitudinally aligned along the length of the suture core and positioned at different points along a length of said surgical suture between first and second ends of said surgical suture, wherein for each of the plurality of sets, the first barb extends outwardly from the core to a free distal end so as to point in a direction toward a first end of the suture and the second barb extends outwardly from the core to a free distal end so as to point in a direction toward a second end of the suture, and the first barb extends outwardly from the core a greater distance than the second barb, has an outer periphery greater than an outer periphery of the second barb and that substantially shields the outer periphery of the second barb when viewed along a longitudinal axis of the core, and is adapted to bend toward the second barb to overlap a sufficient portion of the distal end of the second barb to substantially prevent said second barb from grasping tissue when drawn through said tissue.

9. The surgical suture according to claim 8, wherein at least one of the first and second barbs extend outwardly beyond an outermost dimension of the suture core.

10. The surgical suture according to claim 8, wherein the first barbs extend outwardly beyond an outermost dimension of the suture core, and the second barbs do not extend outwardly beyond an outermost dimension of the suture core.

11. The surgical suture according to claim 10, wherein the second barbs are formed by removing a portion of the suture core.

12. The surgical suture according to claim 8, wherein the first and second barbs are formed by cutting into the suture core.

13. The surgical suture according to claim 8, wherein an underside of at least one of the first and second barbs has one or more extensions projecting outwardly therefrom.

14. The surgical suture according to claim 8, wherein the surgical suture forms part of a braided surgical suture device.

15. The surgical suture according to claim 14, wherein the surgical suture forms a core of the braided surgical suture device.

16. A surgical suture comprising:
a monofilament core extending along a length thereof between a first end and a second end;
a plurality of sets of first and second projections each extending outwardly from the core in a manner such that each set is longitudinally aligned along the length of the core, and positioned at different points along said length between the first and second ends thereof, wherein the first projections extend outwardly from the core to a free distal end so as to point in a direction of a first end of the suture and the second projections extend outwardly from the core to a free distal end so as to point in a direction of a second end of the suture; and
wherein the first projections are sized and shaped, and positioned relative to the second projections so as to extend outwardly from the core a greater distance than the second projections, have an outer periphery greater than an outer periphery of the second projections and that substantially shields the outer periphery of the second projection when viewed along a longitudinal axis of the core, and as so as to be adapted to bend toward the second projections to sufficiently shield the second projections when the surgical suture is drawn through tissue by the second end thereof to thereby substantially prevent said second projection from grasping tissue when drawn therethrough.

17. The suture according to claim 16, wherein the first projections have a larger outer periphery than the respective second projections when viewed along a direction of the core.

18. The suture according to claim 16, wherein an underside of at least one of the first and second projections has one or more extensions extending outwardly therefrom.

19. The suture according to claim 16, wherein the first projections substantially overlap at least a distal tip of the respective second projections when the suture is drawn through tissue by the second end thereof.

\* \* \* \* \*

UNITED STATES PATENT AND TRADEMARK OFFICE
CERTIFICATE OF CORRECTION

PATENT NO. : 8,747,436 B2
APPLICATION NO. : 11/762141
DATED : June 10, 2014
INVENTOR(S) : Nawrocki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1828 days.

Signed and Sealed this
Twenty-eighth Day of July, 2015

Michelle K. Lee
*Director of the United States Patent and Trademark Office*